US010568306B2

(12) United States Patent
De Meester

(10) Patent No.: US 10,568,306 B2
(45) Date of Patent: Feb. 25, 2020

(54) METHOD AND SYSTEM OF GROWING LIVING ORGANISMS

(71) Applicant: DMF SPRL, Marche-en-Famenne (BE)

(72) Inventor: Fabien De Meester, Marche-en-Famenne (BE)

(73) Assignee: DMF SPRL, Marche-en-Famenne (BE)

(*) Notice: Subject to any disclaimer, the term of this patent is extended or adjusted under 35 U.S.C. 154(b) by 677 days.

(21) Appl. No.: 15/301,591

(22) PCT Filed: Mar. 26, 2015

(86) PCT No.: PCT/EP2015/056611
§ 371 (c)(1),
(2) Date: Oct. 3, 2016

(87) PCT Pub. No.: WO2015/150235
PCT Pub. Date: Oct. 8, 2015

(65) Prior Publication Data
US 2017/0172117 A1 Jun. 22, 2017

(30) Foreign Application Priority Data
Apr. 3, 2014 (EP) .................................. 14163346

(51) Int. Cl.
A01K 67/00 (2006.01)
A01K 29/00 (2006.01)
A01K 67/02 (2006.01)
A01G 7/04 (2006.01)

(52) U.S. Cl.
CPC .............. A01K 67/02 (2013.01); A01G 7/045 (2013.01); A01K 29/00 (2013.01); A01K 67/00 (2013.01)

(58) Field of Classification Search
CPC .... A01K 63/06; A01K 63/006; A01K 63/003; A01K 1/03; A01K 61/00; A01K 29/00; A01K 67/02; A01G 7/045
USPC .......................................... 119/300, 267, 174
See application file for complete search history.

(56) References Cited

U.S. PATENT DOCUMENTS

| 4,933,920 A | 6/1990 | Sternberg | |
| 2005/0135104 A1* | 6/2005 | Crabb | A01G 7/045 362/276 |
| 2011/0125296 A1* | 5/2011 | Bucove | A01G 7/045 700/90 |
| 2012/0143381 A1* | 6/2012 | Lawyer | A01K 63/003 700/282 |
| 2014/0041594 A1* | 2/2014 | Plante | A01K 63/003 119/227 |
| 2014/0209035 A1* | 7/2014 | Tang | A01K 1/03 119/267 |
| 2014/0216351 A1* | 8/2014 | Blake | A01K 63/06 119/253 |
| 2015/0136037 A1* | 5/2015 | Boonekamp | A01K 61/00 119/226 |

(Continued)

FOREIGN PATENT DOCUMENTS

WO WO 2010/010540 A1 1/2010

Primary Examiner — Yvonne R Abbott-Lewis
(74) Attorney, Agent, or Firm — Reinhart Boerner Van Deuren P.C.

(57) ABSTRACT

The present invention is related to a method of and a system for growing, maintaining, and/or harvesting living organisms such as plants and/or animals by controlling their physiology and lifetime according to sidereal time, preferably yet not necessarily in phase with sidereal time.

20 Claims, 2 Drawing Sheets

(56) References Cited

U.S. PATENT DOCUMENTS

2016/0037756 A1* 2/2016 Grajcar ................. A01K 63/06
                                                      119/267
2016/0183502 A1* 6/2016 Tanase ................... A01K 63/06
                                                      119/267

* cited by examiner

METHOD AND SYSTEM OF GROWING LIVING ORGANISMS

FIELD OF THE INVENTION

The present invention is related to a method and system of growing, maintaining, and/or harvesting living multicellular (pluricellular) organisms, especially plants and/or animals or a method for modifying the sex ratio (number of females) of new born in an animal population, especially in a poultry or domestic mammals population towards a higher % of females, by controlling (modifying) their physiology and lifetime according to (but not necessarily in phase with) sidereal time.

BACKGROUND OF THE INVENTION AND STATE OF THE ART

Measurement of sidereal time (i.e. the time measured by the rotation of the earth relative to the stars rather than the sun) is important for astronomers and navigators. The sidereal day is the time it takes the earth to make a complete rotation relative to the stars (i.e. the time between the same viewing angle of a particular star on successive nights). It differs from the solar day which is indexed to the sun, and requires that the sun be on a given meridian at the noon hour every day. Thus, the earth rotates about 361 degrees of arc each solar day to maintain this requirement. The earth rotates through that extra degree in about four minutes which makes the solar day about four minutes longer than a sidereal day. Thus sidereal time runs faster than solar time and in fact, the exact factor is 1.00273791 which may be approximated as the ratio of about 2,930/2,922.

Several sidereal time setters such as a sidereal clock (U.S. Pat. No. 4,933,920) is used for a very long time by astronomers and navigators. It exists also watches or clocks indicating simultaneously the mean solar time and the sidereal time.

Recently, it has been discovered that various phenomena affecting animal or human health could have various environmental origins. In particular, it is possible that aging is a time-space phenomenon which at the scale of life on earth is a mind-body phenomenon.

Once realized and understood, the cognitive brain has the ability to take over and counteract aging, i.e. time-space in environmental terms. From the perspective of the sun then the earth progress of about 24 hours/about 365 days or about 4 minutes daily. Say otherwise, the acrophase of all biological systems on earth drifts of about 4 minutes daily or about 1 day yearly. Therefore, on the principle, it may be useful to shift these 4 minutes daily period back in time to use the impact of anti-aging at any age. This phenomenon may affect animals as well as plants possibly feeding these animals, including humans.

SUMMARY OF THE INVENTION

Until now, it has never been proposed to modify the method of growing (including harvesting and maintaining during their all lifetime) living multicellular organisms, especially plants and/or animals, or the method of modifying the sex ratio (number of females) of new born in an animal population, especially in a poultry (laying hens, chicken, quails, geese, turkeys, pigeons (squabs) and domestic ducks or domestic animals (cows, pigs, sheep, goats, horses, donkeys, rabbits, dogs, cats, water buffalos, population by controlling (preferably modifying) their physiology (and/or their lifetime) according to (the dynamic of) sidereal time, preferably in phase with sidereal time. Preferably, this control is obtained by a reduction of 4 minutes difference according to present time, each day for a total of 24 hours every year.

However, such time modification could affect biological parameters (physiology) of living multicellular organisms especially animals, (but also of plants), such as animal diastolic and systolic blood pressure, pulse and heart rate, including health of consumers, especially consumers which will eat these organisms (plants or animals (especially poultry or domestic mammals) having a lifetime (physiology) adapted according to sidereal time.

Figure 1:
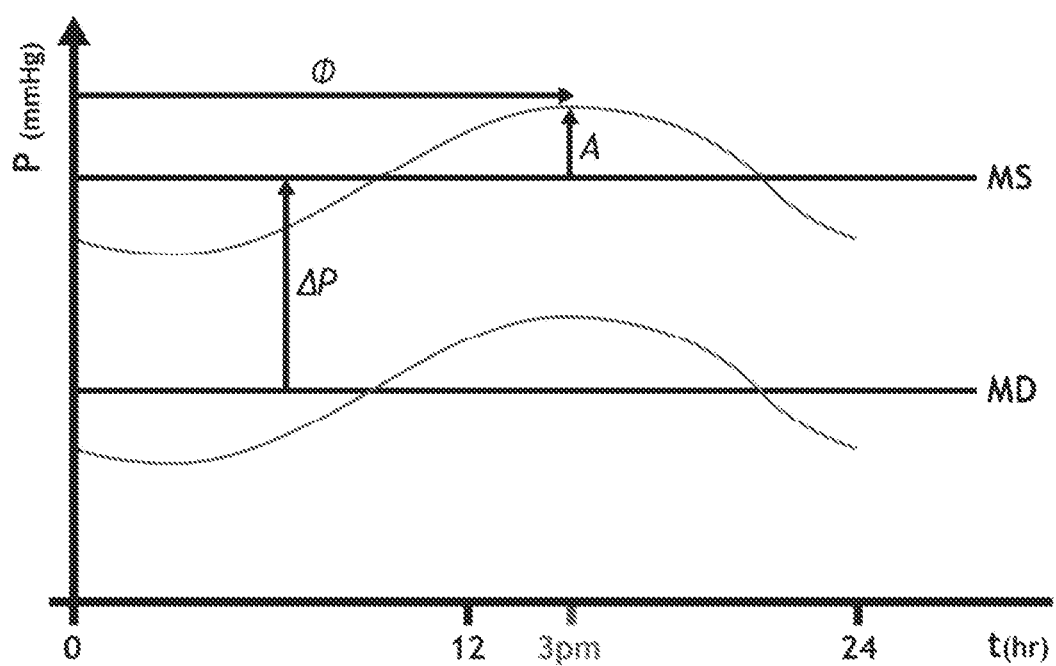
FIG. 1 is a graphical illustration of blood systolic and diastolic pressures with respect to biological systems having imprinted sun dictated ~24 hr-cycles.

As shown in FIG. 1, biological systems have their sun-dictated ~24 hr-cycles imprinted, i.e. here blood systolic (S: upper curve) and diastolic (D: lower curve) pressures. The acrophase ($\varphi$) is the time of the day whereby the variables reach their maximum, and the amplitude (A) is the height of the maximum versus the daily median (M) of the variables (here MS and MD). The rotation of the Earth around the Sun induces a forth-drift in acrophase ($\varphi$) of about 4 minutes daily.

An aim of the present invention consists of maintaining this acrophase ($\varphi$) fixed in time through applying daily a 4 minute period back-drift in time of the time-structure (daylight schedule) controlling such variables and, in turn, biological systems of living multicellular organisms, such as plants and/or animals (especially poultry and domestic animals), including humans.

Any food grown, produced or harvested through applying to the source (physiology of plants and/or animals including food products obtained from these animals, such as eggs and milk) the proposed modified time structure would modify their content profile and will therefore influence the health of consumers eating them.

Furthermore, it is also possible to improve the method of growing living multicellular organisms, such as animals (preferably poultry and domestic mammals) and/or plants, by feeding them and/or providing them with adequate amounts of water or other liquids (milk products, water with minerals, hormones, probiotics, prebiotics and/or antibiotics, . . . ) at specific time intervals adapted according to sidereal time that would improve their physiology (i.e. health and composition, preferably their fatty acids pattern towards a preferred omega-3/omega-6 ratio of 1/1).

In addition, it is also possible to improve the invention method by feeding these animals (preferably poultry and domestic mammals) with improved amount of omega-3 fatty acids, vitamins or other antioxidant compound, prebiotics (fructo-oligosaccharides, . . . ) in their diet and by reducing the amount of omega-6 fatty acids or other lipids (cholesterol, saturated fatty acids, etc.) in their diet administrated according to sidereal time, preferably in phase with sidereal time.

Therefore, the present invention is related to a method and system of growing multicellular organisms (such as animals (preferably poultry and domestic mammals) and/or harvesting multicellular organisms (such as plants) by controlling (or modifying) physiology (and/or lifetime) of these organisms (plants and/or animals) according to (the dynamic of) sidereal time, preferably in phase with sidereal time.

Preferably, in the method and system according to the invention, day-time and night-time lighting conditions of these multicellular organisms (plants and/or animals (preferably poultry and domestic mammals) are controlled (modified) according to sidereal time, preferably in phase with sidereal time.

Therefore, the present invention is related to a method and a system comprising means for controlling (modifying) day-time/night-time lighting conditions of these living organisms (plants and/or animals (preferably poultry and domestic mammals) by using standard-in-the-field array or multiple arrays of energy efficient Light-Emitting Diodes (LEDs) or other lighting systems configured in proximity with plant(s) life and/or animal(s) life to emit light energy, wherein these diodes or these lighting systems are controlled (modified) by a sidereal time setter, preferably a sidereal clock, a sidereal watch or a sidereal chronometer.

The system according to the invention may also comprise other adequate means for performing the method according to the invention, such as a programmable microcontroller connected to this adequate sidereal time setter, for controlling spectral emission and/or feed (or liquid) administration in a designed manner, a software for driving the microcontroller, a memory for storing the software and a power source operably connected to an array of energy efficient light sources, such as Light-Emitting Diodes (LEDs) and/or means for distributing liquids, nutrients or drugs (antibiotics, minerals, probiotics, prebiotics, hormones, . . . ) to these living organisms (animals such as poultry and domestic mammals) and/or plants).

In the system according to the invention, lights emitting diodes are capable of producing useful light with relatively small power consumption and are preferably used because they do not heat and have a very long live. However, other sources of lights could be used for the same purpose.

Advantageously, the system according to the invention could also be linked to specific environmental sensors for controlling (modifying) the efficiency of the growing and/or harvesting method according to the invention and health or growth of the treated organisms (plants and/or animals (including poultry and domestic mammals)).

Preferably, the physiology (and/or life time) of these organisms (plants and/or animals) is controlled (modified) by the sidereal time setter according to the invention, such as defined moments for water or nutrients administration (feed, liquids, hormones, minerals, . . . ).

In addition, the sidereal time setter according to the invention is used to control (modify) other parameters, such as the temperature or hydrometry of the organisms' environment.

Preferably, in the method and system according to the invention, sidereal time is defined by a sidereal time setter preferably selected from the group consisting of a sidereal clock, a sidereal watch or a sidereal chronometer.

EXAMPLE

Figure 2:
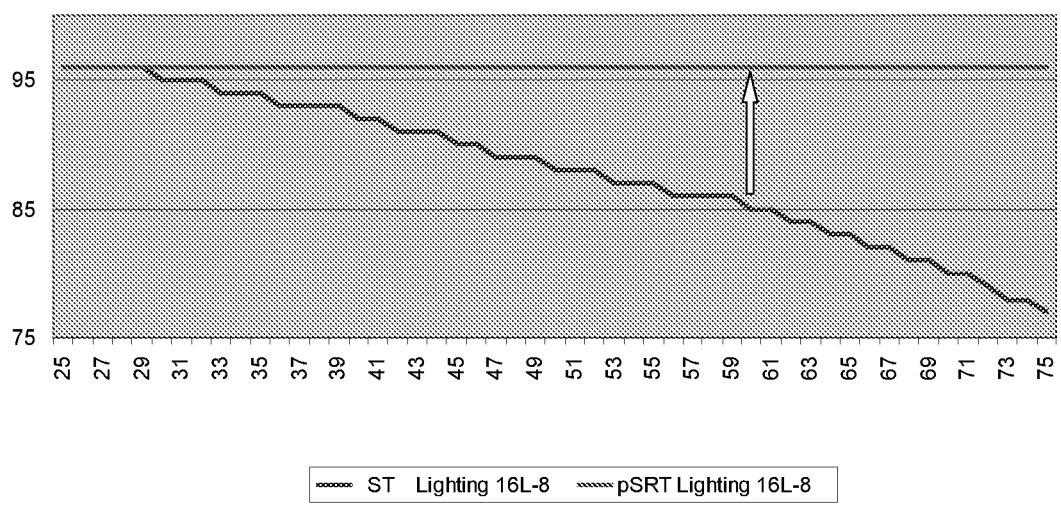
FIG. 2 is a representation of Hy-Line Brown Parent Stock Performance Graph under solar-Standard (sSTD) & pseudoSidereal (pSRT) Lighting Programs (Hen-day egg production (%) according to age (Weeks).

The FIG. 2 represents Hy-Line Brown Parent Stock Performance Graph under solar-Standard (sSTD) & pseudo-Sidereal (pSRT) Lighting Programs (Hen-day egg production (%) according to age (Weeks).
30 Hy-Line Brown breeders (www.hyline.com) were submitted to a pseudo-sidereal lighting program according to the invention (4 min drift back in time daily—using Hy-Line Light Program for Light-Controlled Housing—http://sales.hyline.com/WebLighting/WebLighting.aspx), all other parameters (floor space allowance 13 birds/m$^2$, 8 males/100 females, 16 hours light—8 hours darkness, light intensity 30 Lux & spectra red-orange, feed/water access ad libitum, incubating & hatching egg care program, color sexing) kept constant.

As for laying hens, the anti-aging effect is observed and obvious on the hen's breeding performance (hen-day egg production) with no statistically observable differences noticed on mortality, body weight, feed consumption, average egg weight, and breeding quality (hatchability). The pseudo-sidereal lighting program according to the invention (4 min drift back in time daily) however induces an additional selective sexing advantage as all hatched chicks are unexpectedly female.

SUMMARY OF PERFORMANCE STANDARDS

|  | sSTD | pSRT |
|---|---|---|
| Hen-day egg production (%) @ 25/60/75 wk | 96/85/77 | 96/96/96 |
| Average Hatchability (%) | 78 | 78 |
| Number of Female Chicks Produced/Hatched Egg | 0.5 | 1.0 |

The invention claimed is:

1. A method of growing, maintaining and/or harvesting multicellular living organisms by controlling their physiology and lifetime according to sidereal time, and reducing via the sidereal time about 4 minutes difference according to present time each day, for a total of about 24 hours every year.

2. The method according to the claim 1 of growing, maintaining and/or harvesting multicellular living organisms by controlling their physiology and lifetime in phase with sidereal time.

3. The method according to the claim 1, wherein the living organisms are plants.

4. The method according to the claim 1, wherein the living organisms are animals.

5. The method of claim 4, wherein the animals are selected from the group consisting of poultry and domestic mammals.

6. The method of claim 4, which modify the sex ratio of new born population towards a higher female %.

7. The method of claim 6, wherein the female % in the new born population of animals is higher than 75%.

8. The method according to the claim 6 wherein the female % in the new born population is higher than 90%.

9. The method according to the claim 1, wherein controlling of the multicellular living organisms physiology and lifetime are day-time and night-time lighting conditions of living organisms controlled according to the dynamic of the sidereal time.

10. The method according to the claim 9, wherein living organisms lighting conditions have different light source for desired time interval at desired intensity.

11. The method according to the claim 1, wherein the controlling of living organisms physiology and lifetime are feed or liquid administration to living organisms controlled by the dynamic of the sidereal time.

12. The method according to claim 1, wherein sidereal time is defined by a sidereal time setter selected from the group consisting of a sidereal clock, a sidereal watch or a sidereal chronometer.

13. A system for growing and/or harvesting multicellular living organisms in a controlled environment, which comprises a sidereal time setter for controlling physiology and lifetime of living organisms according to the dynamic of the sidereal time, the sidereal time setter configured for reducing about 4 minutes difference according to present time each day, for a total of about 24 hours every year.

14. The system of claim 13, comprising a sidereal time setter for controlling physiology and lifetime of multicellular living organisms in phase with sidereal time.

15. The system according to the claim 13, wherein the sidereal time controls day-time/night-time lighting conditions of the multicellular living organisms.

16. The system according to the claim 13, wherein the sidereal time setter controls feed or liquid administration to the multicellular living organisms.

17. The system according to the claim 13, wherein the sidereal time setter is selected from the group consisting of a sidereal clock, a sidereal watch or a sidereal chronometer.

18. The system according to the claim 13, wherein the multicellular living organisms are plants.

19. The system according to the claim 13, wherein the multicellular living organisms are animals.

20. The system of claim 19, wherein the animals are selected from the group consisting of poultry or domestic animals.

* * * * *